US00PP29162P2

(12) United States Plant Patent
Egger

(10) Patent No.: US PP29,162 P2
(45) Date of Patent: Mar. 27, 2018

(54) ***HEUCHERA* PLANT NAMED 'TNHEUNEL'**

(50) Latin Name: ***Heuchera* hybrid**
Varietal Denomination: TNHEUNEL

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 11 days.

(21) Appl. No.: 15/330,803

(22) Filed: Nov. 7, 2016

(51) Int. Cl.
*A01H 5/02* (2018.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by yellow to lime colored leaves, medium large, slightly lobed, geranium like leaves, rust red flowers in narrow spikes in spring on upright flowering stems, good sun tolerance, a large, mounding habit with excellent crown count, and excellent vigor.

1 Drawing Sheet

Botanical denomination: *Heuchera* hybrid.
Variety designation: 'TNHEUNEL'.

BACKGROUND OF THE INVENTION

The present invention relates to a new and distinct cultivar of *Heuchera* and given the cultivar name of 'TNHEUNEL'. *Heuchera* is in the family Saxifragaceae. *Heuchera* 'TNHEUNEL' originated as a controlled cross using *Heuchera* 'K803-2', a proprietary, unpatented, unnamed plant as the seed parent, and *Heuchera* 'K803-4', a proprietary, unpatented, unnamed plant as the pollen parent. These parents are a result of breeding using hardy *Heuchera richardsonii* with proprietary hybrid lines. *Heuchera* 'TNHEUNEL' was bred to be a hardy, large, landscape plant.

Compared to the seed parent, *Heuchera* 'K803-2', the new cultivar has a larger habit and the flowers are rust red rather than green.

Compared to the pollen parent, *Heuchera* 'K803-4', the new cultivar has a larger habit.

Compared to *Heuchera* 'Citronelle', U.S. Plant Pat. No. 17,934, the new cultivar has smaller, rounder, thicker, leaves. The flowers of the new cultivar are rust red rather than white.

This new *Heuchera* is uniquely distinguished by:

1. yellow to lime colored leaves,
2. medium large, slightly lobed, geranium like leaves,
3. rust red flowers in narrow spikes in spring on upright flowering stems,
4. good sun tolerance,
5. a large, mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a three year old plant of *Heuchera* 'TNHEUNEL' in flower growing in the trial bed in April in Canby, Oreg.

FIG. 2 shows the same plant in August.

DETAILED PLANT DESCRIPTION

The following is a detailed description of the new *Heuchera* cultivar based on observations taken in April of one-year-old specimens growing in the trial field in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart, 5th* edition, 2007.

Plant:

*Form.*—Basal rosette, herbaceous perennial.
*Hardiness.*—USDA Zone 4 to 9.
*Size.*—27 cm tall from top of the foliage to the ground and 40 cm wide (mature plant grows to 35 cm tall and 58 cm wide).
*Number of crowns.*—About 40.
*Habit.*—Medium large, mounding.
*Vigor.*—Excellent.

Leaf:

*Type*.—Simple.

*Arrangement*.—Rosette.

*Shape*.—Broadly ovate to orbicular.

*Number*.—About 200.

*Blade size*.—Grows to 11.3 cm long and 11.3 cm wide.

*Venation*.—Palmate.

*Lobing/division*.—7 shallow palmate lobes.

*Margins*.—Crenate.

*Apex*.—Mucronulate.

*Base*.—Cordate, strongly overlapping and sometimes spiraling in.

*Surface texture*.—Glandular-puberulent on both sides.

*Leaf rugosity*.—Absent.

*Petiole description*.—Grows to 15 cm long and 3.5 mm wide, glandular hairs, color closest to Yellow Green 145B, tinted Greyed Red 182C at base.

*Leaf color*.—Spring new leaves, top and bottom side including veins Yellow Orange 16B; mature leaves Yellow Green 144A with veins 145C, bottom side Yellow Green 146D with veins 145C.

Inflorescence:

*Size*.—Grows to 4.5 cm wide and 11.5 cm long.

*Type*.—Upright thyrse.

*Number of flowers per thyrse*.—About 110.

*Number of thyrse*.—About 20.

*Peduncle*.—Grows to 38 cm long and 5 mm wide at base, glandular hairs, Yellow Green 146B lightly tinted Greyed Red 178A on top ⅓.

*Pedicel*.—Grows to 3 mm long, with glandular hairs, Greyed Orange 177B.

*Bloom period*.—Late April to June in Canby, Oreg.

Flower bud:

*Size*.—3 mm wide and 5 mm long.

*Description*.—Glandular puberulent, ovoid, down facing.

*Color*.—Greyed Red 182A.

Flower:

*Type*.—Perfect.

*Shape*.—Campanulate.

*Attitude*.—Side and down-facing.

*Size*.—6 mm long and 6 mm wide.

*Corolla description*.—5 petals, each 4 mm long and 1.3 mm wide, spatulate, margins entire, tip acute, glandular-puberulent and Greyed Purple 186B on both sides.

*Calyx description*.—Campanulate, 6 mm long and 6 mm wide, with 5 lobes with wide sinuses divided ½ way to the base, each 2 mm wide and 3 mm long, oblong in shape, back side glandular-puberulent, glabrous inside, tip obtuse, margin entire, Greyed Red 179B on both sides.

*Stamen description*.—5 in number, filaments 2.5 mm long, White NN155A, anthers 1 mm long, Orange 26A, pollen Yellow Orange 16A.

*Pistil description*.—1, 2-beaked, 5 mm long and 2 mm wide, Greyed Red 179C overall, ovary 2 mm long and 2 mm wide, style 2 mm long.

*Fragrance*.—None.

*Lastingness*.—Each thyrse blooms for about 3 weeks on the plant.

Fruit and seed: None seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

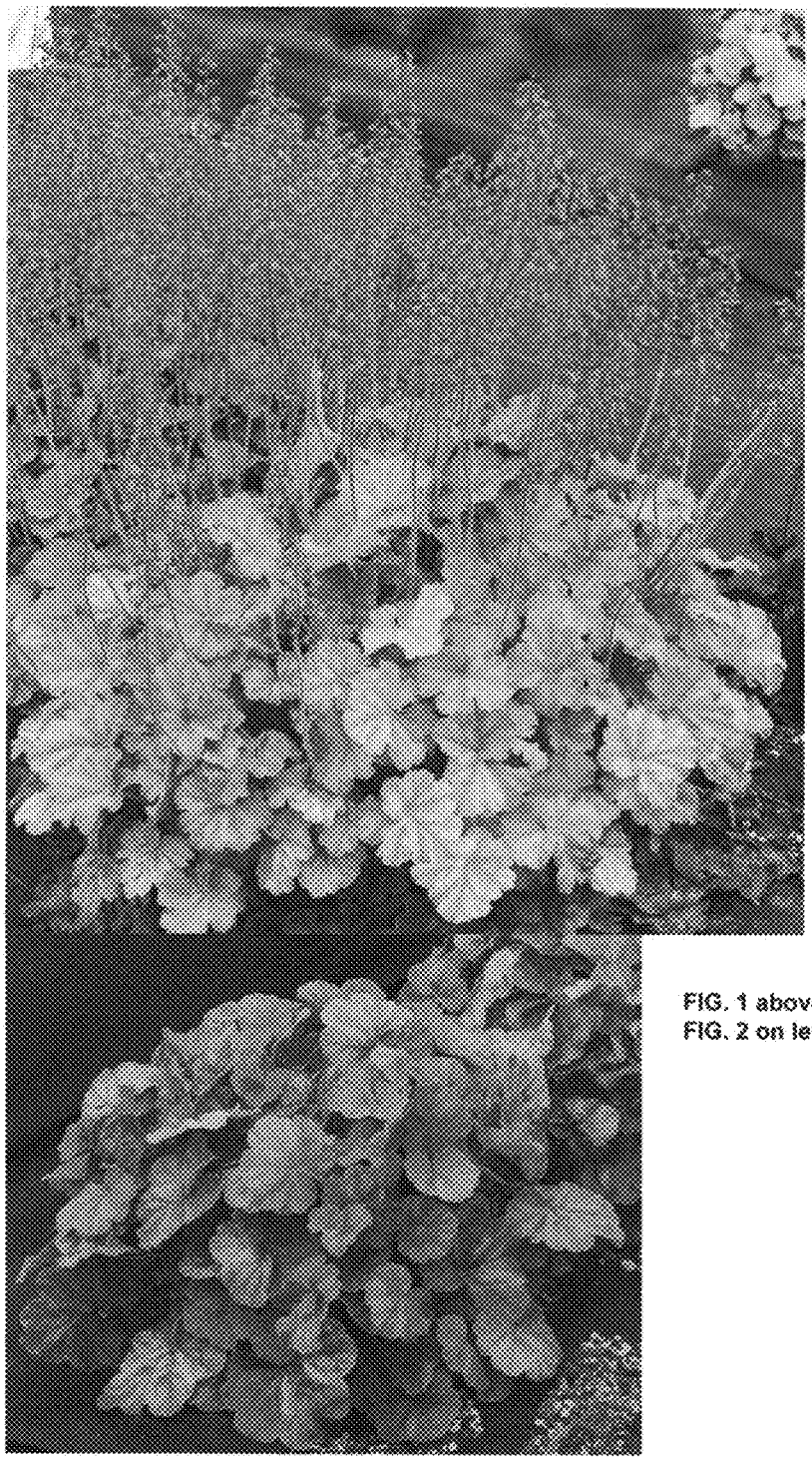
FIG. 1 above
FIG. 2 on left